US008022279B2

(12) United States Patent
Mayer et al.

(10) Patent No.: US 8,022,279 B2
(45) Date of Patent: *Sep. 20, 2011

(54) LIPOSOMAL FORMULATIONS OF ANTHRACYCLINE AGENTS AND CYTIDINE ANALOGS

(75) Inventors: Lawrence Mayer, North Vancouver (CA); Sharon Johnstone, Vancouver (CA); Troy Harasym, North Vancouver (CA)

(73) Assignee: Celator Pharmaceuticals, Inc., Princeton, NJ (US)

( * ) Notice: Subject to any disclaimer, the term of this patent is extended or adjusted under 35 U.S.C. 154(b) by 875 days.

This patent is subject to a terminal disclaimer.

(21) Appl. No.: 11/587,112

(22) PCT Filed: Apr. 22, 2005

(86) PCT No.: PCT/CA2005/000625
§ 371 (c)(1),
(2), (4) Date: Aug. 2, 2007

(87) PCT Pub. No.: WO2005/102359
PCT Pub. Date: Nov. 3, 2005

(65) Prior Publication Data
US 2007/0286897 A1    Dec. 13, 2007

Related U.S. Application Data

(60) Provisional application No. 60/565,210, filed on Apr. 22, 2004.

(51) Int. Cl.
*A61K 9/127* (2006.01)
(52) U.S. Cl. ........................................................ 977/801
(58) Field of Classification Search .................. None
See application file for complete search history.

(56) References Cited

U.S. PATENT DOCUMENTS

| 5,059,421 A | 10/1991 | Loughrey et al. |
| 5,077,056 A | 12/1991 | Bally et al. |
| 5,736,155 A | 4/1998 | Bally et al. |
| 6,146,659 A * | 11/2000 | Rahman .................. 424/450 |
| 2003/0147945 A1 | 8/2003 | Tardi et al. |
| 2004/0052864 A1 | 3/2004 | Rubinfeld et al. |

FOREIGN PATENT DOCUMENTS

| EP | 1 325 739 | 7/2003 |
| WO | WO 03/028697 | * 4/2003 |
| WO | WO-2004/087115 | 10/2004 |
| WO | WO-2004/093795 | 11/2004 |
| WO | WO-2005/000266 | 1/2005 |

OTHER PUBLICATIONS

Spiers et al., British Medical Journal, 1977, 2: 544-547.*
Chang et al., Acta Paediatr. Tw., 2000, 41:294-302.*
Yates et al., Blood, 1982, 60: 454-462.*
Kobayashi et al., Int J Cancer, 1977, 20: 581-587.*
Kim et al., Cancer Treat Rep, 1987, 71: 447-450.*
Murry et al., Ann Pharmacother, 2000, 34: 1173-1178.*
Gokhale et al., British Journal of Cancer (1996) 74(1):43-48.
Supplementary European Search Report for EP 05738885.2, mailed Mar. 4, 2009, 4 pages.
Thigpen, Seminars in Oncology (2002) 29(1, Suppl. 01):11-16.
Vaage et al., International Journal of Cancer (1993) 54(1):959-964.
Celano et al., BMC Cancer (2004) 4:Article 63.
Cortes et al., Cancer (2001) 92:7-14.
Fisher, Clin. Colorectal Cancer (2001) 1(2):85-86.
Fracasso et al., Cancer (2002) 95(10):2223-2229.
Frei et al., Clin. Cancer Res. (1998) 4:2027-2037.
Giles et al., J. Clin. Oncol. (2003) 21(9):1722-1727.
International Search Report for PCT/CA2005/000625, mailed on Aug. 11, 2005, 6 pages.
Rivera et al., J. Clinical Oncology (2001) 19(6):1716-1722.
Rivera et al., J. Clinical Oncology (2003) 21(17):3249-3254.
Rivera, The Oncologist (2003) 8(Suppl 2):3-9.

* cited by examiner

*Primary Examiner* — Ileana Popa
(74) *Attorney, Agent, or Firm* — Morrison & Foerster LLP

(57) ABSTRACT

Compositions which comprise an anthracycline agent, and a cytidine analog are encapsulated in liposomal carriers. The preferred anthracycline agent is selected from the group of daunorubicin, doxorubicin, and idarubicin, while the preferred cytidine analog is selected from the group of cytarabine, gemcitabine, or 5-azacytidine. The combination of the anthracycline agent and cytidine analog encapsulated in said liposomal carriers are useful in achieving a drug retention and a sustained drug release for each therapeutic agent.

14 Claims, 5 Drawing Sheets

LIPOSOMAL FORMULATIONS OF ANTHRACYCLINE AGENTS AND CYTIDINE ANALOGS

CROSS-REFERENCE TO RELATED APPLICATION

This application is the national phase of PCT application PCT/CA2005/000625 having an international filing date of 22 Apr. 2005, which claims benefit under 35 U.S.C. §119(e) to provisional application 60/565,210 filed Apr. 22, 2004, The contents of these documents are incorporated herein by reference.

TECHNICAL FIELD

The invention relates to compositions and methods for improved delivery of combinations of therapeutic agents. More particularly, the invention concerns delivery systems which provide combinations of anthracycline agents and cytidine analogs and derivatives thereof.

BACKGROUND ART

The progression of many life-threatening diseases such as cancer, AIDS, infectious diseases, immune disorders and cardiovascular disorders are influenced by multiple molecular mechanisms. Due to this complexity, achieving cures with a single agent has been met with limited success. Thus, combinations of agents have often been used to combat disease, particularly in the treatment of cancers. It appears that there is a strong correlation between the number of agents administered and cure rates for cancers such as acute lymphocytic leukemia and metastatic colorectal cancer (Frei, et al., *Clin. Cancer Res.* (1998) 4:2027-2037; Fisher, M. D.; *Clin Colorectal Cancer* (2001) August; 1(2):85-6).

Anthracycline antibiotics such as daunorubicin, doxorubicin, epirubicin and their derivatives comprise known antineoplastic agents. Daunorubicin-based drugs, such as daunorubicin hydrochloride, are primarily employed because they intercalate with DNA, affecting various functions of the DNA, including DNA and RNA synthesis. They exhibit activity against acute lymphocytic leukemia, acute granulocytic leukemia, acute myelocytic leukemia, the acute phase of chronic myelocytic leukemia, and acute nonlymphocytic leukemia. Doxorubicin has been shown effective in the treatment of acute leukemias, malignant lymphomas and selected solid tumors such as breast cancer tumors. Idarubicin exhibits similar activity to these antimetabolites and has been used together with cytarabine for adverse karyotype, acute myeloid leukemia (AML). Giles, F. J., et al., *J. Clin. Oncol.* (2003) 21(9):1722-7.

Cytidine analogs, such as three examples of such analogs including cytarabine, 5-Azacytidine, and gemcitabine, are known antineoplastic agents. For example, these compounds have demonstrated effectiveness at inhibiting DNA synthesis in leukemia and cancer cells. These properties have enabled these compounds to effectively treat acute myelocytic leukemia, acute lymphoblastic leukemia and myelodysplastic syndromes, pancreatic cancer and lung cancer.

US 2004/0052864 discusses the administration of a non-encapsulated DNA methylation inhibitor and a nonencapsulated anti-neoplastic agent, either singularly or in a free drug cocktail, for the treatment of diseases associated with abnormal cell proliferation. However, no pharmaceutical preparations designed to control delivery or half-lives of the drugs were suggested in this publication.

Similarly, U.S. Pat. No. 5,736,155 discusses the preparation of liposome encapsulated neoplastic agents. Single and multiple antineoplastic agents are contemplated as administered simultaneously or sequentially, however, the combination of an anthracycline antibiotic together with a cytidine analog was not suggested.

There are various drawbacks that limit the therapeutic use of drug cocktails. For instance, administration of free drug cocktails often results in rapid clearance of one or all of the drugs before reaching the tumor site. For this reason, many drugs have been incorporated into delivery vehicles designed to 'shield' them from mechanisms that would otherwise result in their clearance from the bloodstream. It is well known that liposomes have the ability to provide this 'shielding' effect and they are thus able to extend the half-life of therapeutic agents. However, formulation of specific drugs or more than one drug into delivery vehicles has proven to be difficult because the lipid composition of the vehicle often differentially affects the pharmacokinetics of individual drugs. Thus a composition that is suitable for retention and release of one drug may not be suitable for the retention and release of a second drug.

Investigators of the present invention have identified particular delivery vehicle formulations required to accommodate a combination of an anthracycline and a cytidine analog (including daunorubicin and cytarabine-based derivatives), which result in superior drug retention and sustained drug release of each agent. They have further demonstrated that synergistic ratios of these drugs, when encapsulated in liposomes, can be successfully maintained in the blood compartment over time resulting in enhanced efficacy compared to the free drug cocktail and individual liposomal drugs.

DISCLOSURE OF THE INVENTION

The invention relates to compositions and methods for administering effective amounts of anthracycline and cytidine analog (e.g., daunorubicin, doxorubicin or idarubicin with cytarabine, 5-Azacytidine or gemcitabine) drug combinations using liposomal delivery vehicles that are stably associated therewith at least one anthracycline agent and one cytidine analog-based drug. These compositions allow the two or more agents to be delivered to the disease site in a coordinated fashion, thereby assuring that the agents will be present at the disease site at a desired ratio. This result will be achieved whether the agents are co-encapsulated in a lipid-based delivery vehicle, or are encapsulated in a separate lipid-based delivery vehicles administered such that desired ratios are maintained at the disease site. The pharmacokinetics (PK) of the composition are controlled by the lipid-based delivery vehicles themselves such that coordinated delivery is achieved (provided that the PK of the delivery systems are comparable).

Thus, in one aspect, the invention provides a liposome composition for parenteral administration comprising at least one anthracycline and one cytidine analog associated with the liposomes at therapeutically effective ratios especially those that are non-antagonistic. The therapeutically effective non-antagonistic ratio of the agents is determined by assessing the biological activity or effects of the agents on relevant cell culture or cell-free systems, as well as tumor homogenates from individual patient biopsies, over a range of concentrations. Frequent combinations are daunorubicin with cytarabine, among other cytidine analogs together with daunorubicin, doxorubicin or their derivatives. Also frequently, a combination is provided comprising cytarabine (or another cytidine analog) and an anthracycline comprising daunorubicin, doxorubicin or idarubicin, among other known anthracyclines. Any method which results in determination of a ratio of agents which maintains a desired therapeutic effect may be used.

The composition comprises at least one anthracycline and one cytidine agent in a mole ratio of the anthracycline to the cytidine agent which exhibits a desired biologic effect to relevant cells in culture, cell-free systems or tumor homogenates. Preferably, the ratio is that at which the agents are non-antagonistic. By "relevant" cells, applicants refer to at least one cell culture or cell line which is appropriate for testing the desired biological effect. As these agents are used as antineoplastic agents, "relevant" cells are those of cell lines identified by the Developmental Therapeutics Program (DTP) of the National Cancer Institute (NCI)/National Institutes of Health (NIH) as useful in their anticancer drug discovery program. Currently the DTP screen utilizes 60 different human tumor cell lines. The desired activity on at least one of such cell lines would need to be demonstrated. By "tumor homogenate," the applicant refers to cells generated from the homogenization of patient biopsies or tumors. Extraction of whole tumors or tumor biopsies can be achieved through standard medical techniques by a qualified physician and homogenization of the tissue into single cells can be carried out in the laboratory using a number of methods well-known in the art.

In another aspect, the invention is directed to a method to deliver a therapeutically effective amount of an anthracycline:cytidine analog combination (e.g., daunorubicin:cytarabine) to a desired target by administering the compositions of the invention.

The invention is also directed to a method to deliver a therapeutically effective amount of an anthracycline:cytidine analog combination by administering an anthracycline stably associated with a first delivery vehicle and a cytidine analog stably associated with a second delivery vehicle. The first and second delivery vehicles may be contained in separate vials, the contents of the vials being administered to a patient simultaneously or sequentially. In one embodiment, the ratio of the anthracycline and the cytidine analog is non-antagonistic.

In another aspect, the invention is directed to a method to prepare a therapeutic composition comprising liposomes containing a ratio of at least one anthracycline and one cytidine analog which provides a desired therapeutic effect which method comprises providing a panel of at least one anthracycline and one cytidine analog wherein the panel comprises at least one, but preferably a multiplicity of ratios of said drugs, testing the ability of the members of the panel to exert a biological effect on a relevant cell culture, cell-free system or tumor homogenate over a range of concentrations, selecting a member of the panel wherein the ratio provides a desired therapeutic effect on said cell culture, cell-free system or tumor homogenate over a suitable range of concentrations; and stably associating the ratio of drugs represented by the successful member of the panel into lipid-based drug delivery vehicles. In preferred embodiments, the abovementioned desired therapeutic effect is non-antagonistic.

As further described below, in a preferred embodiment, in designing an appropriate combination in accordance with the method described above, the non-antagonistic ratios are selected as those that have a combination index (CI) of ≦1.1. In further embodiments, suitable liposomal formulations are designed such that they stably incorporate an effective amount of an anthracycline:cytidine analog combination (e.g., daunorubicin:cytarabine) and allow for the sustained release of both drugs in vivo. Preferred formulations contain at least one negatively charged lipid, such as phosphatidylglycerol.

MODES OF CARRYING OUT THE INVENTION[1]

Figure 1A:
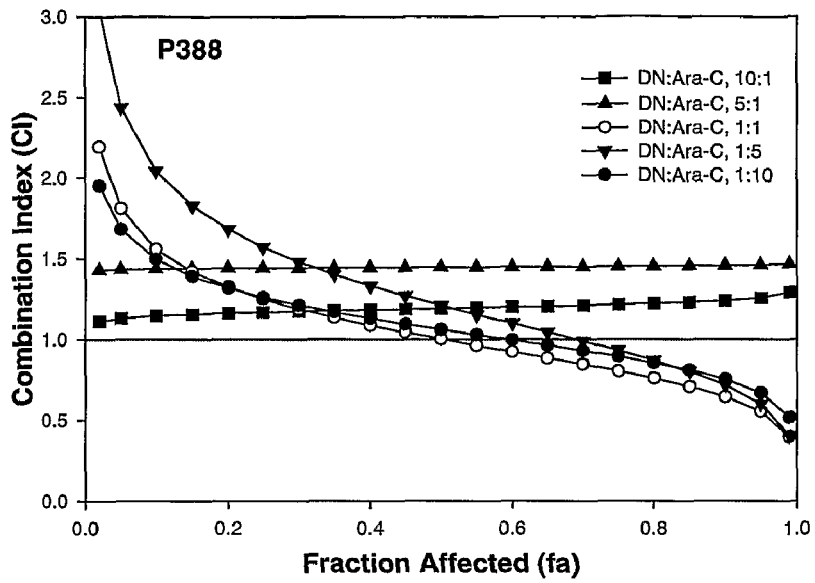
FIG. 1A is a graph showing the combination index (CI) plotted as a function of the fraction of P388 murine lymphocytic leukemia cells affected ($f_a$) by combinations of daunorubicin:cytarabine (or Ara-C) at various mole ratios: 10:1 (squares), 5:1 (triangles), 1:1 (hollow circles), 1:5 (inverted triangles) and 1:10 (filled-in circles).

Unless defined otherwise, all terms of art, notations and other scientific terms or terminology used herein have the same meaning as is commonly understood by one of ordinary skill in the art to which this invention belongs. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

[1]Abbreviations

DSPC: distearoylphosphatidylcholine; PG: phosphatidylglycerol; DSPG: distearoylphosphatidylglycerol; PI: phosphatidylinositol; SM: sphingomyelin; Chol or CH: cholesterol; CHE: cholesteryl hexadecyl ether;

SUV: small unilamellar vesicle; LUV: large unilamellar vesicle; MLV: multilamellar vesicle;

MTT: 3-(4,5-dimethylthiazol-2-yl)-2,5-diphenyl-2H tetrazolium bromide; EDTA: ethylenediaminetetraacetic acid; HEPES: N-[2-hydroxylethyl]-piperazine-N-[2-ethanesulfonic acid]; HBS: HEPES buffered saline (20 mM HEPES, 150 mM NaCl, pH 7.4); SHE: 300 mM sucrose, 20 mM HEPES, 30 mM EDTA; TEA: triethanolamine; CI: combination index; $f_a$: fraction affected.

As used herein, "a" or "an" means "at least one" or "one or more."

The invention provides compositions comprising liposomes stably associated therewith at least one anthracycline antibiotic (e.g., daunorubicin) and one cytosine analog agent (e.g., cytarabine), wherein the anthracycline antibiotic and cytosine analog agent are present at anthracycline antibiotic: cytosine analog agent (e.g., daunorubicin:cytarabine) mole ratios that exhibit a desired cytotoxic, cytostatic or biologic effect to relevant cells or tumor homogenates.

Preferably, liposomal compositions provided herein will include liposomes stably associated therewith at least one anthracycline and one cytidine agent in a mole ratio of the anthracycline:cytidine analog which exhibits a non-antagonistic effect to relevant cells or tumor homogenates.

In further embodiments of the invention, the above described lipid-based delivery vehicles comprise a third or fourth agent. Any therapeutic, diagnostic or cosmetic agent may be included.

In one aspect of the invention, liposomes which comprise phosphatidylcholine are provided, preferably distearoylphosphatidylcholine. In another aspect of the invention, liposomes which comprise a sterol are provided. Preferably the sterol is cholesterol.

The lipid-based delivery vehicles of the present invention may be used not only in parenteral administration but also in topical, nasal, subcutaneous, intraperitoneal, intramuscular, aerosol or oral delivery or by the application of the delivery vehicle onto or into a natural or synthetic implantable device at or near the target site for therapeutic purposes or medical imaging and the like. Preferably, the lipid-based delivery vehicles of the invention are used in parenteral administration, most preferably, intravenous administration.

The preferred embodiments herein described are not intended to be exhaustive or to limit the scope of the invention to the precise forms disclosed. They are chosen and described to best explain the principles of the invention and its application and practical use to allow others skilled in the art to comprehend its teachings.

Cytidine Analogs

Antimetabolites or, more particularly, cytidine analogs such as cytarabine, 5-Azacytidine, and gemcitabine (2',2'-Difluorodeoxycytidine) are known antineoplastic agents. Cytidine analogs may also be referred to in the art as cytosine nucleoside analogs. Antimetabolites are compounds that are similar enough to a natural chemical to participate in a normal biochemical reaction in cells but different enough to interfere with the normal division and functions of cells. These compounds generally inhibit a normal metabolic process.

Cytarabine is a pyrimidine nucleoside antimetabolite. This compound is an analog of 2'-deoxycytidine with the 2'-hydroxyl in a position trans to the 3'-hydroxyl of the sugar. Cytarabine is considered equivalent with 4-Amino-1-β-d-arabinofuranosyl-2(1H)-pyrimidinone, 1-β-d-arabinofuranosylcytosine, Ara-C, β-cytosine arabinoside, aracytidine, CHX-3311, U-19920, Alexan, Arabitin, Aracytine, Cytarbel, Cytosar, Erpalfa, Iretan and Udicil. In cytidine analogs such as cytarabine, the sugar moiety comprises an arabinose rather than ribose. Cytarabine is recognized as useful in the therapy of acute myelocytic leukemia (AML) and has proven effectiveness in the remission of this disorder. However, the mechanism of action of cytarabine is uncertain, nevertheless incorporation of this nucleotidase into DNA leads to an inhibition of polymerization by termination of strand synthesis.

Cytarabine must be "activated" via conversion of the 5-monophosphate nucleotide (AraCMP) to terminate strand synthesis. AraCMP is then able to react with selected nucleotide kinases to form diphosphate and triphosphate nucleotides (AraCDP and AraCTP). Cytarabine incorporation into DNA is S-phase specific, thus dosing has been advocated over at least one full cell cycle to obtain inhibition of DNA synthesis. Inhibition of DNA synthesis occurs at low AraCTP concentrations and inhibits DNA chain elongation by incorporation of AraC into the terminal portion of a growing DNA chain. Moreover, there appears to be a correlation between the amount of AraC incorporated into the chain and the inhibition of DNA synthesis.

Subjects can develop resistance to cytarabine. Such resistance is generally due to a deficiency of deoxycytidine kinase, which produces AraCMP. In addition, degrative enzymes such as cytidine deaminase (which deaminates AraC to nontoxic arauridine) and dCMP (which converts AraCMP to inactive AraUMP) also affect efficacy.

A drawback of cytarabine is its toxicity. This compound is a potent myleosuppresive agent capable of producing severe leucopenia, thrombocytopenia and anemia with notable megaloblastic changes. Gastrointestinal disturbances, fever, conjunctivitis, pneumonitis, hepatic dysfunction, dermatitis, and neurotoxic side effects have also been noted generally when higher doses are administered.

5-Azacytidine (Azacytidine; 5-AzaC) is a compound that exhibits antineoplastic activity. This compound is known as useful for the treatment of AML, acute lymphoblastic leukemia and myelodysplastic syndromes. Current studies are evaluating the effects of this compound in beta thalassemia, acute myeloid leukemia, myelodysplastic syndrome, advanced or metastatic solid tumors, non-Hodgkin's lymphoma, multiple myeloma, non-small cell lung cancer and prostate cancer. 5-AzaC has been shown to inhibit DNA methylation, which in turn affects gene expression. Side effects include decreased white and red blood cell and platelet count, nausea, vomiting, fatigue, diarrhea, among other effects.

Gemcitabine is a nucleoside analog that exhibits antitumor activity. Gemcitabine HCl consists of a 2'-deoxy-2',2'-difluorocytidine monohydrochloride ($\beta$-isomer) and is known as effective in treating pancreatic cancer and lung cancer. In general, gemcitabine prevents cells from making DNA and RNA by interfering with the synthesis of nucleic acids. This action stops the growth of cancer cells, causing the cells to die. Side effects include decreased white blood cell and platelet count, nausea, vomiting, fatigue, diarrhea, flu-like symptoms, rashes, among other effects.

Anthracycline Antibiotics

Anthracycline antibiotics such as daunorubicin and doxorubicin and their derivatives comprise known antineoplastic agents produced by the fungus *Streptomyces peucetius*. Idarubicin (4-demethoxydaunorubicin) comprises a synthetic derivative of daunorubicin lacking the methoxy group on C4 of the aglycone ring. These compounds intercalate with DNA, affecting various functions of the DNA, including DNA and RNA synthesis. The interaction with DNA generally causes single and/or double strand breaks and sister chromatid exchange. One particular pharmaceutical form of daunorubicin (daunorubicin hydrochloride) has been demonstrated to prevent cell division in doses that do not interfere with nucleic acid synthesis. The mechanism by which the scission of the DNA is accomplished is not fully understood, but it is believed to be mediated by the action of topoisomerase II or by the generation of free radicals. Moreover, anthracyclines are also known to interact with cell membranes and alter their functions, which may play a role in their antitumor actions cardiotoxicity.

Daunorubicin (daunomycin, rubidomycin, leukaemomycin C, RP-13057, CERUBIDINE®) is known as useful in the treatment of acute lymphocytic leukemia, acute granulocytic leukemia, acute myelocytic leukemia, the acute phase of chronic myelocytic leukemia, and acute nonlymphocytic leukemia. In addition, this compound has been demonstrated to have some activity in solid tumors and against lymphomas. Daunorubicin is a glycoside formed by a tatrasysclic agycone-daunomycinone, and an amino sugar-daunosamine. Oral absorption of daunorubicin is low, and it is most frequently administered intravenously. The half-life of distribution is 45 minutes and 19 hours for elimination. Daunorubicin is eliminated via conversion to a less active form, daunorubicinol. Daunorubicin and its derivatives have certain toxicities such as bone marrow depression, stomatitis, alopecia, gastrointestinal disturbances, cardiac dysrhythmias, pulmonary edema. The most widely recognized drawback of these compositions is the potential for cardiomyopathy in acute or chronic forms which can quickly become a life-threatening situation. Cardiotoxicity, in particular, manifests itself as congestive heart failure in 15-40% of patients undergoing therapy. Generally, such side effects are due to the dosage utilized, with the occurrence increasing at higher does. It has been recognized, however, that concomitant administration of dexrazoxane (ADR-529) or amifostine (WR-2721 or WP-1065) will reduce cardiac damage caused by these compositions. Moreover, there is evidence to suggest that cardiac damage during anthracycline therapy can be reduced by simultaneous administration of the iron chelators such as dipyridoxyl and aminopolycarboxylic acid based chelating agents, and their metal chelates. See U.S. Pat. No. 6,147,094.

Doxorubicin (adriamycin, rubrex, 12-naphthacenedione, 14-hydroxydaunomycin, NSC-123127) differs from daunorubicin only in having a hydroxyacetyl group in place of the acetyl group in daunorubicin, in position 8. Doxorubicin has been shown effective in the treatment of acute leukemias, malignant lymphomas and selected solid tumors such as breast cancer tumors. This composition has been utilized together with cyclophosphamide, vincristine and procarbazine in the treatment of Hodgkin's disease and non-Hodgkin's lymphoma. Additional therapeutic utilities have been demonstrated for sarcomas, plasma cell myeloma, metastatic thyroid carcinoma, gastric carcinoma, broncheogenic carcinoma, transitional cell carcinoma, and carcinomas of the ovary, endometrium, thyroid, testes and cervix. The toxicities of doxorubicin are similar to daunorubicin set out above. Analogs of doxorubicin, such as epirubicin (4'-epidoxorubicin), morpholino derivatives and related anthracenedione mitoxantrone, have been shown to have less cardiac toxicity with high clinical activity.

Determining Non-Antagonistic Daunorubicin:Cytarabine Ratios In Vitro

In a further aspect of the invention anthracycline agents and cytidine analogs will be encapsulated into liposomes at synergistic or additive (i.e. non-antagonistic) ratios. Determination of ratios of agents that display synergistic or additive combination effects may be carried out using various algorithms, based on the types of experimental data described below. These methods include isobologram methods (Loewe, et al., *Arzneim-Forsch* (1953) 3:285-290; Steel, et al., *Int. J. Radiol. Oncol. Biol. Phys.* (1979) 5:27-55), the fractional product method (Webb, Enzyme and Metabolic Inhibitors (1963) Vol. 1, pp. 1-5. New York: Academic Press), the Monte Carlo simulation method, CombiTool, ComboStat and the Chou-Talalay median-effect method based on an equation described in Chou, *J. Theor. Biol.* (1976) 39:253-276; and Chou, *Mol. Pharmacol.* (1974) 10:235-247). Alternatives include surviving fraction (Zoli, et al., *Int. J. Cancer* (1999) 80:413-416), percentage response to granulocyte/macrophage-colony forming unit compared with controls (Pannacciulli, et al., *Anticancer Res.* (1999) 19:409-412) and others (Berenbaum, *Pharmacol. Rev.* (1989) 41:93-141; Greco, et al., *Pharmacol Rev.* (1995) 47:331-385).

The Chou-Talalay median-effect method is preferred. The analysis utilizes an equation wherein the dose that causes a particular effect, $f_a$, is given by:

$$D=D_m[f_a/(1-f_a)]^{1/m}$$

in which D is the dose of the drug used, $f_a$ is the fraction of cells affected by that dose, $D_m$ is the dose for median effect signifying the potency and m is a coefficient representing the shape of the dose-effect curve (m is 1 for first order reactions).

This equation can be further manipulated to calculate a combination index (CI) on the basis of the multiple drug effect equation as described by Chou and Talalay, *Adv. Enzyme Reg.* (1984) 22:27-55; and by Chou, et al., in: *Synergism and Antagonism in Chemotherapy*, Chou and Rideout, eds., Academic Press: New York 1991:223-244. A computer program (CalcuSyn) for this calculation is found in Chou and Chou ("Dose-effect analysis with microcomputers: quantitation of ED50, LD50, synergism, antagonism, low-dose risk, receptor ligand binding and enzyme kinetics": CalcuSyn Manual and Software; Cambridge: Biosoft 1987).

The combination index equation is based on the multiple drug-effect equation of Chou-Talalay derived from enzyme kinetic models. An equation determines only the additive effect rather than synergism and antagonism. However, according to the CalcuSyn program, synergism is defined as a more than expected additive effect, and antagonism as a less than expected additive effect. Chou and Talalay in 1983 proposed the designation of CI=1 as the additive effect, thus from the multiple drug effect equation of two drugs, we obtain:

$$CI=(D)_1/(D_x)_1+(D)_2/(D_x)_2 \quad \text{[Eq. 1]}$$

for mutually exclusive drugs that have the same or similar modes of action, and it is further proposed that $$CI=(D)_1/(D_x)_1+(D)_2/(D_x)_2+((D)_1(D)_2)/(D_x)_1(D_x)_2 \quad \text{[Eq. 2]}$$

for mutually non-exclusive drugs that have totally independent modes of action. CI<1, =1, and >1 indicates synergism, additive effect, and antagonism, respectively. Equation 1 or equation 2 dictates that drug 1, $(D)_1$, and drug 2, $(D)_2$, (in the numerators) in combination inhibit x % in the actual experiment. Thus, the experimentally observed x % inhibition may not be a round number but most frequently has a decimal fraction. $(D_x)_1$ and $(D_x)_2$ (in the denominators) of equations 1 and 2 are the doses of drug 1 and drug 2 alone, respectively, inhibiting x %.

For simplicity, mutual exclusivity is usually assumed when more than two drugs are involved in combinations (CalcuSyn Manual and Software; Cambridge: Biosoft 1987).

A two-drug combination may be further used as a single pharmaceutical unit to determine synergistic or additive interactions with a third agent. In addition, a three-agent combination may be used as a unit to determine non-antagonistic interactions with a fourth agent, and so on.

Figure 1B:
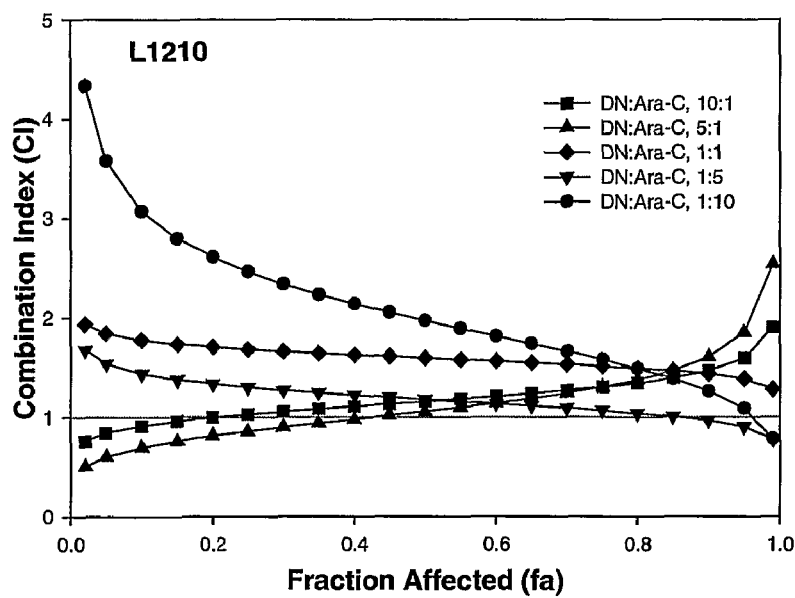
FIG. 1B is a graph showing the combination (CI) plotted as a function of the fraction of L1210 murine lymphocytic leukemia cells affected ($f_a$) by combinations of daunorubicin:cytarabine (or Ara-C) at various mole ratios: 10:1 (squares), 5:1 (triangles), 1:1 (diamonds), 1:5 (inverted triangles) and 1:10 (circles).

The underlying experimental data are generally determined in vitro using cells in culture or cell-free systems. Preferably, the combination index (CI) is plotted as a function of the fraction of cells affected ($f_a$) as shown in FIGS. 1A and 1B which, as explained above, is a surrogate parameter for concentration range. Preferred combinations of agents are those that display synergy or additivity over a substantial range of $f_a$ values. Combinations of agents are selected if non-antagonistic over at least 5% of the concentration range wherein greater than 1% of the cells are affected, i.e., an $f_a$ range greater than 0.01. Preferably, a larger portion of overall concentration exhibits a favorable CI; for example, 5% of an $f_a$ range of 0.2-1.0. More preferably 10% of this range exhibits a favorable CI. Even more preferably, 20% of the $f_a$ range, preferably over 50% and most preferably over at least 70% of the $f_a$ range of 0.2 to 1.0 are utilized in the compositions. Combinations that display synergy over a substantial range of $f_a$ values may be re-evaluated at a variety of agent ratios to define the optimal ratio to enhance the strength of the non-antagonistic interaction and increase the $f_a$ range over which synergy is observed.

While it would be desirable to have synergy over the entire range of concentrations over which cells are affected, it has been observed that in many instances, the results are considerably more reliable in an $f_a$ range of 0.2-0.8 when using a spectrophotometric method such as the MTT assay detailed in Example 1. Thus, although the synergy exhibited by combinations of the invention is set forth to exist within the broad range of 0.01 or greater, it is preferable that the synergy be established in the $f_a$ range of 0.2-0.8. Other more sensitive assays, however, can be used to evaluate synergy at $f_a$ values greater than 0.8, for example, bioluminescence or clonogenecity assays.

The optimal combination ratio may be further used as a single pharmaceutical unit to determine synergistic or additive interactions with a third agent. In addition, a three-agent combination may be used as a unit to determine non-antagonistic interactions with a fourth agent, and so on.

As set forth above, the in vitro studies on cell cultures will be conducted with "relevant" cells. The choice of cells will depend on the intended therapeutic use of the agent. Only one relevant cell line or cell culture type need exhibit the required non-antagonistic effect in order to provide a basis for the compositions to come within the scope of the invention.

For example, in one preferred embodiment of the invention, the combination of agents is intended for anticancer therapy. In a frequent embodiment, the combination of agents is intended for leukemia or lymphoma therapy. Appropriate choices will then be made of the cells to be tested and the nature of the test. In particular, tumor cell lines are suitable subjects and measurement of cell death or cell stasis is an appropriate end point. As will further be discussed below, in the context of attempting to find suitable non-antagonistic combinations for other indications, other target cells and criteria other than cytotoxicity or cell stasis could be employed.

For determinations involving antitumor agents, cell lines may be obtained from standard cell line repositories (NCI or ATCC for example), from academic institutions or other organizations including commercial sources. Preferred cell lines would include one or more selected from cell lines identified by the Developmental Therapeutics Program of the NCI/NIH. The tumor cell line screen used by this program currently identifies 60 different tumor cell lines representing leukemia, melanoma, and cancers of the lung, colon, brain, ovary, breast, prostate and kidney. The required non-antagonistic effect over a desired concentration range need be shown only on a single cell type; however, it is preferred that at least two cell lines exhibit this effect, more preferably three cell lines, more preferably five cell lines, and more preferably 10 cell lines. The cell lines may be established tumor cell lines or primary cultures obtained from patient samples. The cell lines may be from any species but the preferred source will be mammalian and in particular human. The cell lines may be genetically altered by selection under various laboratory conditions, and/or by the addition or deletion of exogenous genetic material. Cell lines may be transfected by any gene-transfer technique, including but not limited to, viral or plasmid-based transfection methods. The modifications may include the transfer of cDNA encoding the expression of a specific protein or peptide, a regulatory element such as a promoter or enhancer sequence or antisense DNA or RNA. Genetically engineered tissue culture cell lines may include lines with and without tumor suppressor genes, that is, genes such as p53, pTEN and p16; and lines created through the use of dominant negative methods, gene insertion methods and other selection methods. Preferred tissue culture cell lines that may be used to quantify cell viability, e.g., to test antitumor agents, include, but are not limited to, P388, L1210, HL-60, MOLT-4, KBM-3, WeHi-3, H460, MCF-7, SF-268, HT29, HCT-116, LS180, B16-F10, A549, Capan-1, CAOV-3, IGROV1, PC-3, MX-1 and MDA-MB-231.

In one preferred embodiment, the given effect ($f_a$) refers to cell death or cell stasis after application of a cytotoxic agent to a cell culture. Cell death or viability may be measured, for example, using the following methods:

| CYTOTOXICITY ASSAY | REFERENCE |
|---|---|
| MTT assay | Mosmann, J. Immunol. Methods (1983) 65(1-2): 55-63. |
| Trypan blue dye exclusion | Bhuyan, et al., Experimental Cell Research (1976) 97: 275-280. |
| Radioactive tritium ($^3$H)-thymidine incorporation or DNA intercalating assay | Senik, et al., Int. J. Cancer (1975) 16(6): 946-959. |
| Radioactive chromium-51 release assay | Brunner, et al., Immunology (1968) 14: 181-196. |
| Glutamate pyruvate transaminase, creatine phosphokinase and lactate dehydrogenase enzyme leakage | Mitchell, et al., J. of Tissue Culture Methods (1980) 6(3&4): 113-116. |
| Neutral red uptake | Borenfreund and Puerner, Toxicol. Lett. (1985) 39: 119-124. |
| Alkaline phosphatase activity | Kyle, et al., J. Toxicol. Environ. Health (1983) 12: 99-117. |
| Propidium iodide staining | Nieminen, et al., Toxicol. Appl. Pharmacol. (1992) 115: 147-155. |
| Bis-carboxyethyl-carboxyfluorescein (BCECF) retention | Kolber, et al., J. Immunol. Methods (1988) 108: 255-264. |
| Mitochondrial membrane potential | Johnson, et al., Proc. Natl. Acad. Sci. USA (1980) 77: 990-994. |
| Clonogenic Assays | Puck, et al., J. of Experimental Medicine (1956) 103: 273-283. |
| LIVE/DEAD Viability/Cytotoxicity assay | Morris, Biotechniques (1990) 8: 296-308. |
| Sulforhodamine B (SRB) assays | Rubinstein, et al., J. Natl. Cancer Instit. (1990) 82: 1113-1118. |

Non-antagonistic ratios of two or more agents can be determined for disease indications other than cancer and this information can be used to prepare therapeutic formulations of two or more drugs for the treatment of these diseases. With respect to in vitro assays, many measurable endpoints can be selected from which to define drug synergy, provided those endpoints are therapeutically relevant for the specific disease.

As set forth above, the in vitro studies on cell cultures will be conducted with "relevant" cells. The choice of cells will depend on the intended therapeutic use of the agent. In vitro studies on individual patient biopsies or whole tumors can be conducted with "tumor homogenate," generated from homogenization of the tumor sample(s) into single cells.

In one preferred embodiment, the given effect ($f_a$) refers to cell death or cell stasis after application of a cytotoxic agent to a "relevant" cell culture or "tumor homogenate" (see Example 1). Cell death or viability may be measured using a number of methods known in the art.

Preparation of Lipid-Based Delivery Vehicles

Preferred lipid carriers for use in this invention are liposomes. Liposomes can be prepared as described in *Liposomes: Rational Design* (A. S. Janoff, ed., Marcel Dekker, Inc., New York, N.Y.), or by additional techniques known to those knowledgeable in the art. Suitable liposomes for use in this invention include large unilamellar vesicles (LUVs), multilamellar vesicles (MLVs), small unilamellar vesicles (SUVs) and interdigitating fusion liposomes.

Liposomes for use in this invention may be prepared to contain a phosphatidylcholine lipid, such as distearylphosphatidylcholine. Liposomes of the invention may also contain a sterol, such as cholesterol. Liposomes may also contain therapeutic lipids, which examples include ether lipids, phosphatidic acid, phosphonates, ceramide and ceramide analogs, sphingosine and sphingosine analogs and serine-containing lipids.

Liposomes may also be prepared with surface stabilizing hydrophilic polymer-lipid conjugates such as polyethylene glycol-DSPE, to enhance circulation longevity. The incorporation of negatively charged lipids such as phosphatidylglycerol (PG) and phosphatidylinositol (PI) may also be added to liposome formulations to increase the circulation longevity of the carrier. These lipids may be employed to replace hydrophilic polymer-lipid conjugates as surface stabilizing agents. Preferred embodiments of this invention may make use of liposomes containing phosphatidylglycerol (PG) or phosphatidylinositol (PI) to prevent aggregation thereby increasing the blood residence time of the carrier.

In one embodiment, liposome compositions in accordance with this invention are preferably used to treat cancer. Delivery of encapsulated drugs to a tumor site is achieved by administration of liposomes of the invention. Preferably liposomes have a diameter of less than 300 nm. Most preferably liposomes have a diameter of less than 200 nm. Tumor vasculature is generally leakier than normal vasculature due to fenestrations or gaps in the endothelia. This allows delivery vehicles of 200 nm or less in diameter to penetrate the discontinuous endothelial cell layer and underlying basement membrane surrounding the vessels supplying blood to a tumor. Selective accumulation of the delivery vehicles into tumor sites following extravasation leads to enhanced anticancer drug delivery and therapeutic effectiveness.

Various methods may be utilized to encapsulate active agents in liposomes. "Encapsulation," includes covalent or non-covalent association of an agent with the lipid-based delivery vehicle. For example, this can be by interaction of the agent with the outer layer or layers of the liposome or entrapment of an agent within the liposome, equilibrium being achieved between different portions of the liposome. Thus encapsulation of an agent can be by association of the agent by interaction with the bilayer of the liposomes through covalent or non-covalent interaction with the lipid components or entrapment in the aqueous interior of the liposome, or in equilibrium between the internal aqueous phase and the bilayer. "Loading" refers to the act of encapsulating one or more agents into a delivery vehicle.

Encapsulation of the desired combination can be achieved either through encapsulation in separate delivery vehicles or within the same delivery vehicle. Where encapsulation into separate liposomes is desired, the lipid composition of each liposome may be quite different to allow for coordinated pharmacokinetics. By altering the vehicle composition, release rates of encapsulated drugs can be matched to allow desired ratios of the drugs to be delivered to the tumor site. Means of altering release rates include increasing the acyl-chain length of vesicle forming lipids to improve drug retention, controlling the exchange of surface grafted hydrophilic polymers such as PEG out of the liposome membrane and incorporating membrane-rigidifying agents such as sterols or sphingomyelin into the membrane. It should be apparent to those skilled in the art that if a first and second drug are desired to be administered at a specific drug ratio and if the second drug is retained poorly within the liposome composition of the first drug (e.g., DMPC/Chol), that improved pharmacokinetics may be achieved by encapsulating the second drug in a liposome composition with lipids of increased acyl chain length (e.g., DSPC/Chol). When encapsulated in separate liposomes, it should be readily accepted that ratios of anthracycline agents-to-cytidine analogs that have been determined on a patient-specific basis to provide optimal therapeutic activity can be generated for individual patients by combining the appropriate amounts of each liposome-encapsulated drug prior to administration. Alternatively, two or more agents may be encapsulated within the same liposome.

Techniques for encapsulation are dependent on the nature of the delivery vehicles. For example, therapeutic agents may be loaded into liposomes using both passive and active loading methods. Passive methods of encapsulating active agents in liposomes involve encapsulating the agent during the preparation of the liposomes. This includes a passive entrapment method described by Bangham, et al. (*J. Mol. Biol.* (1965) 12:238). This technique results in the formation of multilamellar vesicles (MLVs) that can be converted to large unilamellar vesicles (LUVs) or small unilamellar vesicles (SUVs) upon extrusion. Another suitable method of passive encapsulation includes an ether injection technique described by Deamer and Bangham (*Biochim. Biophys. Acta* (1976) 443:629) and the Reverse Phase Evaporation technique as described by Szoka and Paphadjopoulos (*P.N.A.S.* (1978) 75:4194). In addition, another suitable method of passive encapsulation involves passive equilibration after the formation of liposomes. This process involves incubating preformed liposomes under altered or non-ambient (based on temperature, pressure, etc.) conditions and adding a therapeutic agent (e.g., cytidine analog or anthracycline agent) to the exterior of the liposomes. The therapeutic agent then equilibrates into the interior of the liposomes, across the liposomal membrane. The liposomes are then returned to ambient conditions and unencapsulated therapeutic agent, if present, is removed via dialysis or another suitable method.

Active methods of encapsulation include the pH gradient loading technique described in U.S. Pat. Nos. 5,616,341, 5,736,155 and 5,785,987 and active metal-loading. One method of pH gradient loading is the citrate-base loading method utilizing citrate as the internal buffer at a pH of 4.0 and a neutral exterior buffer. Other methods employed to establish and maintain a pH gradient across a liposome involve the use of an ionophore that can insert into the liposome membrane and transportions across membranes in exchange for protons (see U.S. Pat. No. 5,837,282). A recent and preferred technique utilizing transition metals to drive the uptake of drugs into liposomes via complexation in the absence of an ionophore may also be used. This technique relies on the formation of a drug-metal complex rather than the establishment of a pH gradient to drive uptake of drug.

Passive and active methods of entrapment may also be coupled in order to prepare a liposome formulation containing more than one encapsulated agent.

Administering Compositions of the Invention In Vivo

As mentioned above, the delivery vehicle compositions of the present invention may be administered to warm-blooded animals, including humans as well as to domestic avian species. For treatment of human ailments, a qualified physician will determine how the compositions of the present invention should be utilized with respect to dose, schedule and route of administration using established protocols. Such applications may also utilize dose escalation should agents encapsulated in delivery vehicle compositions of the present invention exhibit reduced toxicity to healthy tissues of the subject.

Preferably, the pharmaceutical compositions of the present invention are administered parenterally, i.e., intraarterially, intravenously, intraperitoneally, subcutaneously, or intramuscularly. More preferably, the pharmaceutical compositions are administered intravenously or intraperitoneally by a bolus or infusional injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578, incorporated by reference.

In other methods, the pharmaceutical or cosmetic preparations of the present invention can be contacted with the target tissue by direct application of the preparation to the tissue. The application may be made by topical, "open" or "closed" procedures. By "topical", it is meant the direct application of the multi-drug preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Alternatively, the preparations may be administered through endoscopic devices.

Pharmaceutical compositions comprising delivery vehicles of the invention are prepared according to standard techniques and may comprise water, buffered water, 0.9% saline, 0.3% glycine, 5% dextrose, iso-osmotic sucrose solutions and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the delivery vehicle suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

Preferably, the pharmaceutical compositions of the present invention are administered intravenously. Dosage for the delivery vehicle formulations will depend on the ratio of drug to lipid and the administrating physician's opinion based on age, weight, and condition of the patient.

In addition to pharmaceutical compositions, suitable formulations for veterinary use may be prepared and administered in a manner suitable to the subject. Preferred veterinary subjects include mammalian species, for example, non-human primates, dogs, cats, cattle, horses, sheep, and domesticated fowl. Subjects may also include laboratory animals, for example, in particular, rats, rabbits, mice, and guinea pigs.

Kits

The therapeutic agents in the invention compositions may be formulated separately in individual compositions wherein each therapeutic agent is stably associated with appropriate delivery vehicles. These compositions can be administered separately to subjects as long as the pharmacokinetics of the delivery vehicles are coordinated so that the ratio of therapeutic agents administered is maintained at the target for treatment. Thus, it is useful to construct kits which include, in separate containers, a first composition comprising delivery vehicles stably associated with at least a first therapeutic agent and, in a second container, a second composition comprising delivery vehicles stably associated with at least one second therapeutic agent. The containers can then be packaged into the kit.

The kit will also include instructions as to the mode of administration of the compositions to a subject, at least including a description of the ratio of amounts of each composition to be administered. Alternatively, or in addition, the kit is constructed so that the amounts of compositions in each container is pre-measured so that the contents of one container in combination with the contents of the other represent the correct ratio. Alternatively, or in addition, the containers may be marked with a measuring scale permitting dispensation of appropriate amounts according to the scales visible. The containers may themselves be useable in administration; for example, the kit might contain the appropriate amounts of each composition in separate syringes. Formulations which comprise the pre-formulated correct ratio of therapeutic agents may also be packaged in this way so that the formulation is administered directly from a syringe prepackaged in the kit.

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

EXAMPLES

Example 1

Daunorubicin:Cytarabine Synergy In Vitro is Drug Ratio Dependent

Many combinations of two or more drugs have the ability to exhibit synergistic effects. Similarly, combinations of the same two or more drugs may also show additive or antagonistic interactions. In order to identify ratios of daunorubicin and cytarabine (also known as, Ara-C) that are synergistic, various combinations of daunorubicin and cytarabine were tested for their cytotoxic effects in vitro. More specifically, drug ratios that demonstrate synergy over a broad range of drug concentrations were identified.

Measuring additive, synergistic or antagonistic effects was performed using daunorubicin:cytarabine (DN:Ara-C) at 10:1, 5:1, 1:1, 1:5 and 1:10 mole ratios in P388 and L1210 murine lymphocytic leukemia cells. The standard tetrazolium-based calorimetric MTT cytotoxicity assay protocol (Mosmann, et al., J. Immunol Methods (1983) 65(1-2):55-63) was utilized to determine the readout for the fraction of cells affected. Briefly, viable cells reduce the tetrazolium salt, 3-(4, 5-diethylthiazoyl-2-yl)-2,5-diphenyltetrazolium bromide (MTT) to a blue formazan which can be read spectrophotometrically. Cells, such as the P388 or L1210 murine lymphocytic leukemia cells used here, are passaged in BDF-1 mice and are removed, as required, and transferred into 75 cm2 flasks in fresh cell culture medium and added into 96-well cell culture plates at a concentration of 10,000 or 6,000 P388 or L1210 cells per well, respectively, in 100 μL per well. The cells are then allowed to incubate for 24 hours at 37° C., 5% $CO_2$ and >75% humidity to promote cell adhesion. The following day, serial drug dilutions are prepared in 12-well cell culture plates. The agents, previously prepared in various solutions, are diluted in fresh cell culture media. Agents are administered to the appropriate wells for single agents (20 μL) and at specific fixed ratio dual agent combinations (increments of 20 μL). The total well volumes are made up to 200 μL with fresh media. The drug exposure is for a duration of 72 hours.

Following drug exposure, MTT reagent (1 mg/mL phosphate buffered salt solution) is added to each well at a volume of 50 μL per well and incubated for 4 hours. The well contents are then aspirated and 150 μL of dimethylsulfoxide (DMSO) is added to each well to disrupt the cells and to solubilize the formazan precipitate within the cells. The 96-well plates are shaken on a plate shaker for a minimum of 2 minutes, and read on a microplate spectrophotometer set at a wavelength of 570 nm. The optical density (OD) readings are recorded and the OD values of the blank wells containing media alone are subtracted from all the wells containing cells. The cell survival following exposure to agents is based as a percentage of the control wells cells not exposed to drug. All wells are performed in triplicate and mean values are calculated.

Figure 1C:
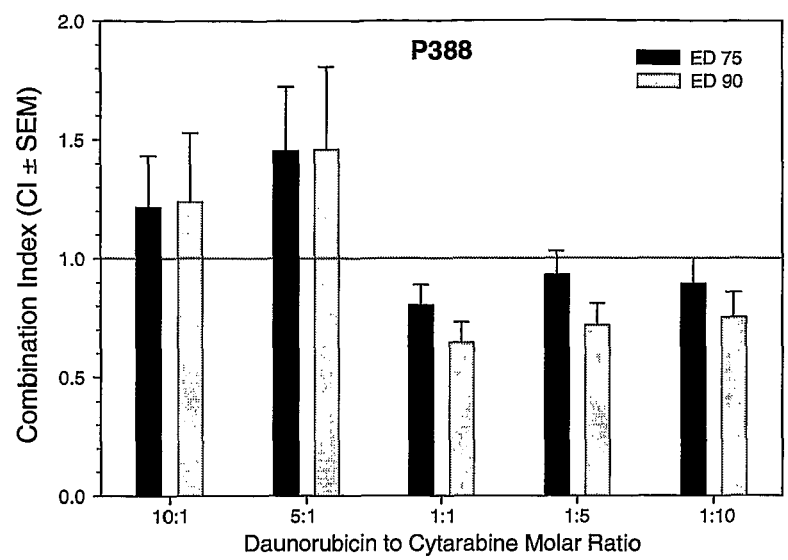
FIG. 1C is a graph showing the CI versus various mole ratios of daunorubicin:cytarabine (10:1, 5:1, 1:1, 1:5, 1:10) in P388 murine lymphocytic leukemia cells. CI values at drug concentrations sufficient to cause 75% (ED75) and 90% (ED90) tumor cell growth inhibition are compared at the different daunorubicin:cytarabine molar ratios.
Figure 1D:
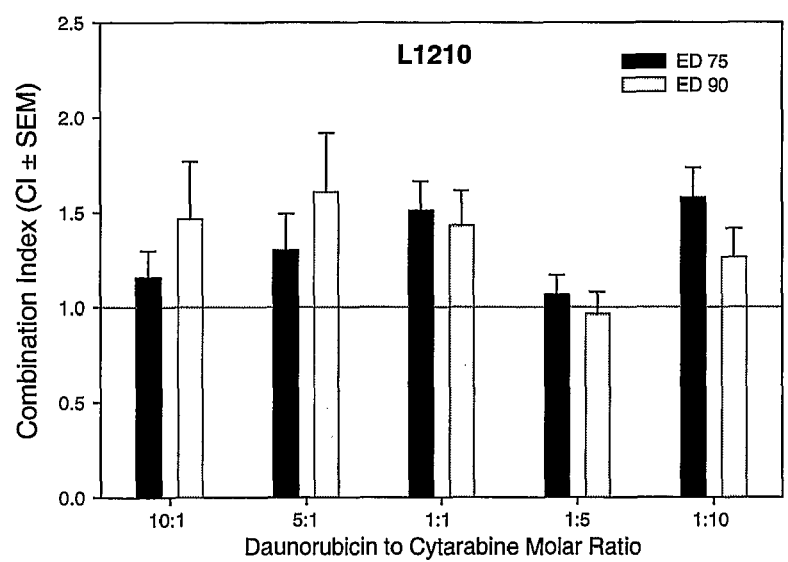
FIG. 1D is a graph showing the CI versus various mole ratios of daunorubicin:cytarabine (10:1, 5:1, 1:1, 1:5, 1:10) in L1210 murine lymphocytic leukemia cells. CI values at drug concentrations sufficient to cause 75% (ED75) and 90% (ED90) tumor cell growth inhibition are compared at the different daunorubicin:cytarabine molar ratios.

A combination index was then determined for each daunorubicin:cytarabine dose using Calcusyn which is based on Chou and Talalay's theory of dose-effect analysis, in which a "median-effect equation" has been used to calculate a number of biochemical equations that are extensively used in the art. Derivations of this equation have given rise to higher order equations such as those used to calculate Combination Index (CI). As mentioned previously, CI can be used to determine if combinations of more than one drug and various ratios of each combination are antagonistic (CI>1.1), additive (0.9<CI>1.1) or synergistic (CI<0.9). CI plots are typically illustrated with CI representing the y-axis versus the proportion of cells affected, or fraction affected ($f_a$), on the x-axis. The data in FIGS. 1A and 1B, plotted as CI versus the fraction of P388 or L1210 murine lymphocytic leukemia cells affected ($f_a$), respectively, illustrates that particular combinations of daunorubicin and cytarabine are antagonistic while others are synergistic or additive. At daunorubicin:cytarabine (DN:Ara-C) ratios of 1:10, 1:5 and 1:1, synergy is observed in P388 cells at $f_a$ values of 0.75 and above (FIG. 1A). This demonstrates that a 1:1, 1:10 and 1:5 ratio are synergistic at concentrations sufficient to cause significant tumor cell kill. The 1:5 and 1:10 ratios or daunorubicin:cytarabine are also non-antagonistic in L1210 cells over a suitable range of $f_a$ values (FIG. 1B). In contrast, 5:1 and 10:1 ratios of daunorubicin:cytarabine are antagonistic in P388 and L1210 cells over a broad range of $f_a$ values. The dependence of CI on daunorubicin:cytarabine ratio is also presented in FIGS. 1C and 1D where CI values at drug concentrations sufficient to cause 75% (ED75) and 90% (ED90) tumor cell growth inhibition are compared at the different daunorubicin:cytarabine molar ratios in P388 and L1210 cells. Based on these results, a mole ratio of 1:5 daunorubicin:cytarabine was selected for formulating in fixed drug ratio liposome carriers.

Example 2

Daunorubicin and Cytarabine can be Dual-Loaded into Liposomes

Liposomes containing both daunorubicin and cytarabine could be generated using DSPC/DSPG/Cholesterol (7:2:1 mole ratio) liposomes containing passively entrapped cytarabine which were actively loaded with daunorubicin. Briefly, lipid foams were prepared by dissolving lipids (DSPC:DSPG:CHOL (7:2:1 mol ratio)) mixed at a concentration of 100 mg lipid/ml final concentration into a chloroform:methanol:H$_2$0 mixture (95:4:1 vol/vol). The solvent was then removed by vacuum evaporation and the resulting lipid foams were hydrated with a solution consisting of 100 mM Cu(gluconate)$_2$, 220 mM triethanolamine (TEA), pH 7.4 and 50 mg/mL (203 mM) cytarabine (containing $^3$H-cytarabine as a tracer) at 70° C. The resulting MLVs were extruded 10 times at 70° C. to generate large unilamellar vesicles. The mean diameter of the resulting liposomes was determined by QELS (quasi-elastic light scattering) analysis to be approximately 100 nm+/−20 nm. Subsequently, the liposomes were buffer exchanged into 300 mM sucrose, 20 mM HEPES, 1 mM EDTA (SHE), pH 7.4, using tangential flow dialysis, thereby removing any unencapsulated cytarabine and Cu(gluconate)$_2$/TEA. Cytarabine to lipid molar ratios were determined using liquid scintillation counting to determine lipid concentration ($^{14}$C-DPPC) and cytarabine concentration ($^3$H-Cytarabine).

Daunorubicin was added to these liposomes to a final target daunorubicin:cytarabine molar ratio of 1:5. Daunorubicin loading into the liposomes was facilitated by incubating the samples at 50° C. for 30 minutes. After loading, the sample was cooled to room temperature. Drug encapsulation efficiency was evaluated after liposome elution through a sephadex G-50 spin column.

Daunorubicin loading efficiency was determined using absorbance at 480 nm against a standard curve. A drug to lipid ratio at each time point was determined using absorbance at 480 nm for daunorubicin measurement and liquid scintillation counting to determine lipid concentrations. Table 1 shows the mean daunorubicin/lipid ratio and cytarabine/lipid ratio after drug encapsulation and removal of free drug. It is apparent from Table 1 that daunorubicin, added at an initial daunorubicin to lipid ratio of 0.042:1, can be efficiently loaded into DSPC/DSPG/Chol (7:2:1 mole ratio) liposomes, containing passively entrapped cytarabine at a 0.234 drug to lipid ratio.

TABLE 1

Daunorubicin:Cytarabine co-loaded in DSPC:DSPG:CHOL (7:2:1 mol:mol) liposomes.

| Daunorubicin; lipid molar ratio | Cytarabine; lipid molar ratio | Daunorubicin:cytarabine ratio |
|---|---|---|
| 0.0418 +/− 0.0041 | 0.234 +/− 0.0239 | 0.178 +/− 0.013 |

Data represents the mean +/− standard deviation, n = 10.

Example 3

Maintaining Ratios of Drugs In Vivo

To determine if daunorubicin and cytarabine could be maintained at the 1:5 drug:drug ratio in the synergistic range in vivo, DSPC/DSPG/Chol (7:2:1 mol:mol), liposomes containing encapsulated daunorubicin and cytarabine were administered intravenously to mice and the plasma drug/drug ratio was monitored over time.

Briefly, lipid foams were prepared by dissolving lipids mixture (DSPC:DSPG:CHOL (7:2:1 mol ratio)) at a concentration of 100 mg lipid/ml final concentration into a chloroform:methanol:H$_2$0 mixture (95:4:1 vol/vol). The solvent was then removed by vacuum evaporation and the resulting lipid foams were hydrated with a solution consisting of 100 mM Cu(gluconate)$_2$, 220 mM triethanolamine (TEA), pH 7.4 and 50 mg/mL (203 mM) of cytarabine (containing trace amounts of $^3$H-cytarabine) at 70° C. The resulting MLVs were extruded at 70° C. to generate large unilamellar vesicles. The mean diameter of the resulting liposomes was determined by QELS (quasi-elastic light scattering) analysis to be approximately 100 nm+/−20 nm. Subsequently, the liposomes were buffer exchanged into, 300 mM sucrose, 20 mM sodium phosphate, 10 mM EDTA, pH 7.4, and then into 300 mM sucrose, 20 mM sodium phosphate, pH 7.4, using tangential flow dialysis, thus removing any unencapsulated cytarabine and Cu(gluconate)$_2$/TEA.

Daunorubicin was added to these liposomes such that the daunorubicin to cytarabine final molar ratio would be about 1:5. Daunorubicin loading into the liposomes was facilitated by incubating the samples at 50° C. for 30 minutes. After loading, the sample was cooled to room temperature. Drug encapsulation efficiency was evaluated after liposome elution through a Sephadex G-50 spin column. Cytarabine to lipid ratios were determined using liquid scintillation counting to determine lipid concentrations ($^{14}$C-DPPC) and cytarabine concentrations ($^3$H-cytarabine). Daunorubicin loading efficiency was measured using absorbance at 480 nm against a standard curve. The drug to lipid ratio was determined using absorbance at 480 nm for daunorubicin measurement and liquid scintillation counting to determine lipid and cytarabine concentrations.

The preparation was then injected intravenously via the tail vein into BDF-1 mice. Doses of the liposomal formulations were 5 mg/kg of daunorubicin and 12.5 mg/kg of cytarabine. At the indicated time points after intravenous administration, blood was collected by cardiac puncture (3 mice per time point) and placed into EDTA coated micro containers. The samples were centrifuged to separate plasma, and plasma was transferred to another tube. Daunorubicin and cytarabine plasma levels were quantified with High Performance Liquid Chromatography (HPLC).

Figure 2A:
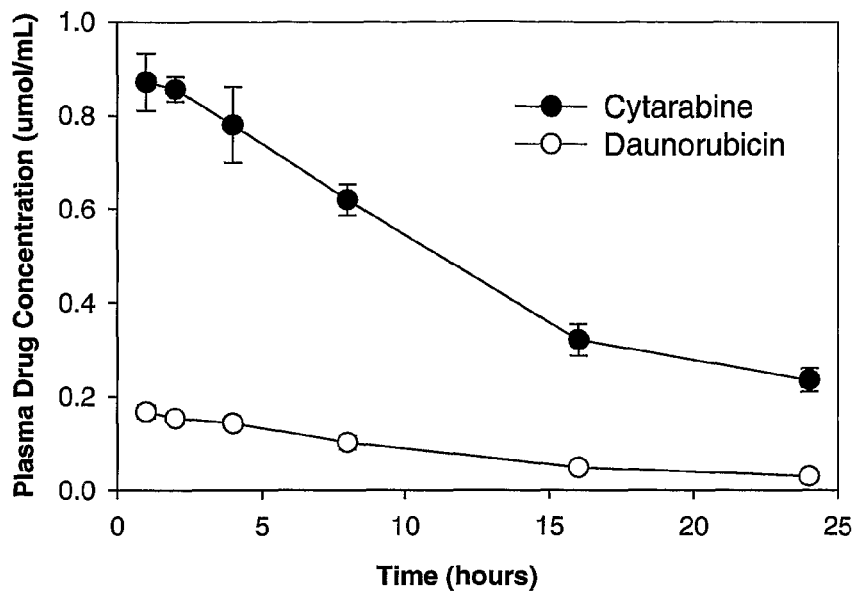
FIG. 2A is a graph showing the plasma elimination curves for daunorubicin and cytarabine at various time points after intravenous administration to BDF-1 mice in DSPC:DSPG:CHOL (7:2:1 mol ratio) liposomes.

FIG. 2A shows that plasma elimination curves for daunorubicin and cytarabine at various time points after intravenous administration to BDF-1 mice when they were delivered in the above-described liposomes. One-hour post iv injection the daunorubicin plasma concentration was 167 nmol/ml and a concentration of 872 nmol cytarabine/ml plasma was observed. At four hours post injection the daunorubicin concentration was 143 nmol/ml and the cytarabine concentration was 781 nmol/ml.

Figure 2B:
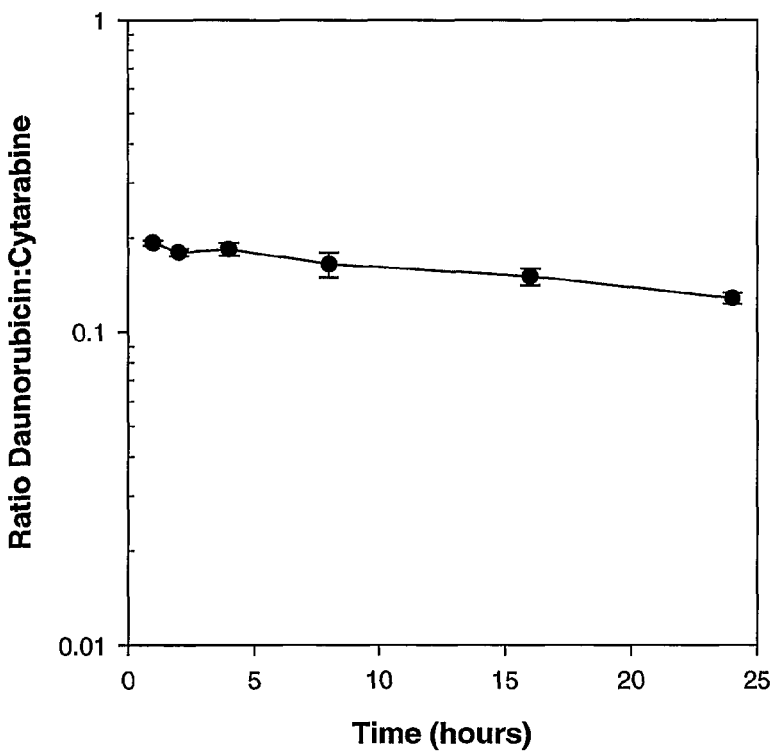
FIG. 2B is a graph of the daunorubicin:cytarabine ratio (mol:mol) in the plasma as a function of time after intravenous administration of daunorubicin:cytarabine (about 1:5 molar ratio) dual-loaded DSPC:DSPG:CHOL (7:2:1 mol ratio) liposomes. Data points represent the molar ratios of daunorubicin:cytarabine determined in plasma (+/−standard deviation) at the specified time points.

FIG. 2B shows that plasma levels of daunorubicin and cytarabine were effectively maintained in a synergistic range for extended time after intravenous administration to BDF-1 mice when the drugs were simultaneously delivered in the above-described liposomes. Data points represent the molar ratios of daunorubicin:cytarabine determined in plasma (+/− standard deviation) at the specified time points. Therefore, appropriately designed delivery vehicles such as liposomes can deliver the desired ratio of daunorubicin and cytarabine in vivo.

Example 4

Daunorubicin and Cytarabine Co-Formulated in Liposomes at a Synergistic Ratio Demonstrates Superior Antitumor Efficacy To maximize the therapeutic activity of drug combinations and to capture the synergistic benefits observed in vitro, the drug combination needs to be delivered to the tumors site at the optimal drug to drug ratio. A single liposome formulation containing the two drugs at fixed ratios known to be synergistic in tissue culture was developed allowing co-ordinate in vivo drug release as illustrated in example 3. The antitumor activity of this formulation was then evaluated in P388 and L1210 murine lymphocytic leukemia models.

DSPC/DSPG/Chol (7:2:1 mole ratio) liposomes co-encapsulated with daunorubicin and cytarabine at a synergistic molar ratio of approximately 1:5 were prepared as described in Example 3.

In order to perform tumor studies on mice, animals are inoculated ip with $1\times10^6$ P388 or L1210 tumors cells which were then allowed to grow for 24 hr prior to initiation of treatment. Mice were organized into appropriate treatment groups consisting of control and treatment groups including saline, liposomal Daunorubicin, liposomal Cytarabine, free drug cocktail and daunorubicin:cytarabine co-loaded in DSPC:DSPG:Chol (7:2:1, mol:mol) liposomes resulting in a final daunorubicin:cytarabine molar ratio of approximately 1:5. Mice were injected intravenously with the required volume of sample to administer the prescribed dose to the animals based on individual mouse weights on days 1, 4 and 7 post tumor cell inoculations. Animals were weighted and monitored for survival and in-life observations are collected at the time of weight measurement. FIG. 3 illustrates the results of these experiments.

Figure 3A:
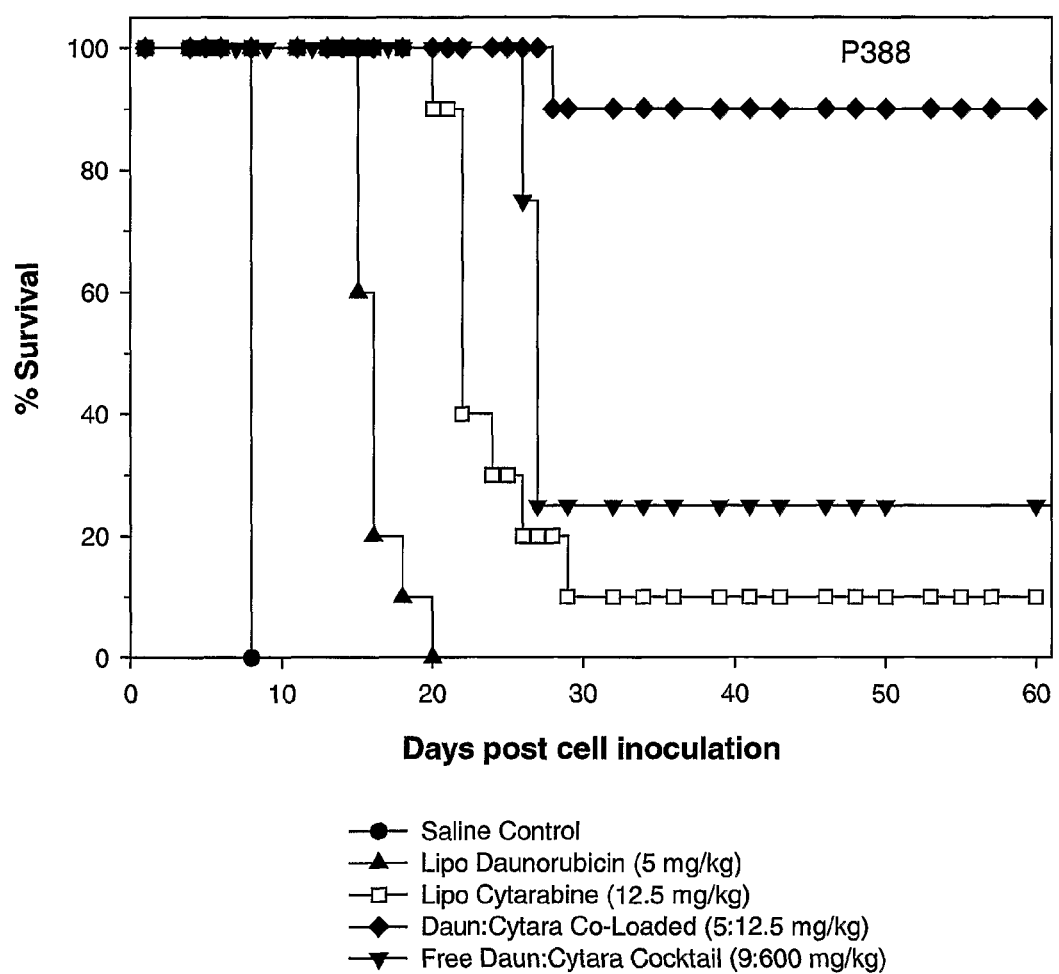
FIG. 3A is a graph showing the efficacy of co-loaded liposome entrapped daunorubicin:cytarabine (about 1:5 mol ratio) compared to individual liposomal encapsulated drugs and free drug cocktail administered via i.v. (Q3DX3) against the P388 lymphocytic leukemia model in mice. Mice were organized into appropriate treatment groups consisting of control and treatment groups including saline (circles), liposomal daunorubicin (triangles), liposomal cytarabine (squares), free cocktail of daunorubicin:cytarabine (9:600 mg/kg) (inverted triangles) and daunorubicin:cytarabine co-loaded in DSPC:DSPG:Chol (7:2:1, mol:mol) liposomes resulting in a final daunorubicin:cytarabine molar ratio of about 1:5 (diamonds).

As FIG. 3A indicates, a significantly enhanced antitumor activity for the liposome formulation containing daunorubicin:cytarabine co-loaded at about a 1:5 molar ratio was observed compared to each single agent formulated individually into liposomes, as well as free drug cocktail administered at its maximum tolerated dose (MTD). The buffer control group had a median survival time of 8 days. The animals treated with liposomal daunorubicin at a dose of 5 mg/kg exhibited a median survival time of 16 days corresponding to an increase in survival time of 100%. The mice treated with liposomal cytarabine at 12.5 mg/kg displayed a median survival time of 22 days corresponding to an increase in survival time of 175% and the mice treated with daunorubicin and cytarabine co-loaded at about a 1:5 molar drug ratio inside DSPC:DSPG:Chol (7:2:1, mol:mol) liposomes exhibited a median survival time of >60 days and increase in life span of >650% with 9/10 long term survivors. In comparison, the mice treated with the daunorubicin:cytarabine as a free drug cocktail at its MTD (based on maximizing dose of both free drugs) did not respond as well to the antitumor therapy as reflected by the median survival time of 27 days and the corresponding increase in life span of 237%.

Figure 3B:
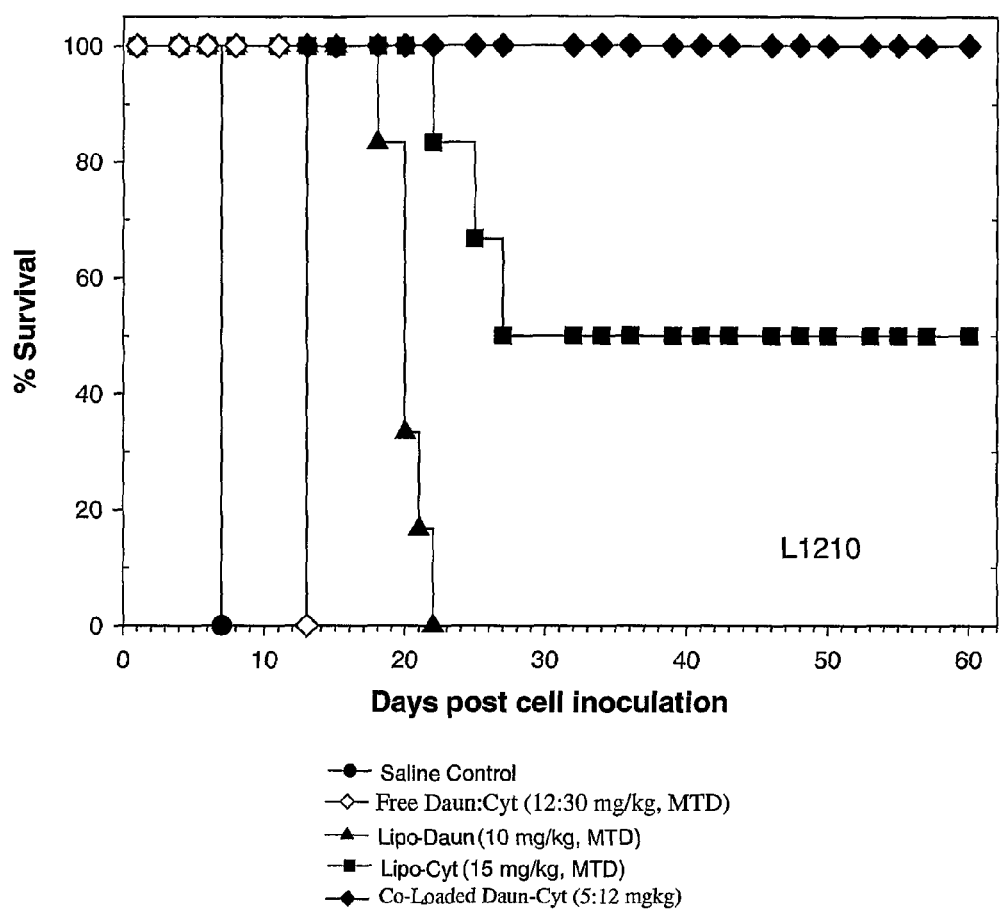
FIG. 3B is a graph showing the efficacy of co-loaded liposome entrapped daunorubicin:cytarabine (about 1:5 mol ratio) compared to individual liposomal encapsulated drugs and free cocktail administered via i.v. (Q3DX3) against the L1210 lymphocytic leukemia model in mice. Mice were organized into appropriate treatment groups consisting of control and treatment groups including saline (circles), liposomal daunorubicin (triangles), liposomal cytarabine (squares), free cocktail of daunorubicin:cytarabine (12:30 mg/kg) (open diamonds) and daunorubicin:cytarabine co-loaded in DSPC:DSPG:Chol (7:2:1, mol:mol) liposomes resulting in a final daunorubicin:cytarabine molar ratio of about 1:5 (filled diamonds).

Similarly, as seen in FIG. 3B, superior antitumor activity was achieved for the liposome formulation with daunorubicin and cytarabine co-loaded at about a 1:5 molar ratio as compared to either the corresponding free drug cocktail or each drug loaded in a liposome individually. The buffer control group had a median survival time of 7 days. Mice treated with either liposome-encapsulated daunorubicin or liposome-encapsulated cytarabine had a median survival time of 20 and 43.5 days, respectively. In comparison, the animals treated with daunorubicin and cytarabine co-loaded at a molar ratio of about 1:5 into DSPC/DSPG/Chol (7:2:1 mol ratio) liposomes exhibited a median survival time of greater than 60 days.

These results demonstrate that fixing synergistic daunorubicin:cytarabine ratios by encapsulating them inside appropriately designed liposomes can dramatically improve antitumor activity.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

Citation of the above publications or documents is not intended as an admission that any of the foregoing is pertinent prior art, nor does it constitute any admission as to the contents or date of these publications or documents.

We claim:

1. A composition for parenteral administration to a subject which composition comprises liposomes having associated therewith daunorubicin and cytarabine in a mole ratio of daunorubicin:cytarabine of about 1:5 wherein the daunorubicin and cytarabine are associated with the liposomes so that said mole ratio is maintained in the blood for at least one hour after administration to the subject.

2. The composition of claim 1, wherein the daunorubicin and cytarabine are co-encapsulated.

3. The composition of claim 1, wherein the liposomes have a mean diameter of between 4.5 and 500 nm.

4. The composition of claim 3, wherein the liposomes have a mean diameter of less than 250 nm.

5. The composition of claim 1, wherein the liposomes comprise a phosphatidylcholine-containing lipid, and/or a charged lipid and/or a sterol.

6. The composition of claim 5, wherein the liposomes comprise DSPC, DSPG and cholesterol in a mole ratio of about 7:2:1.

7. A method to treat a leukemia in a subject which comprises administering to said subject an effective amount of the composition of claim 1.

8. The method of claim 7, wherein the subject is a human.

9. The method of claim 7, wherein the subject is a non-human mammal or avian.

10. The method of claim 8, wherein the leukemia is ALL or AML.

11. The composition of claim 1, wherein the composition comprises no therapeutic agents additional to the daunorubicin and cytarabine.

12. The composition of claim 1, wherein the daunorubicin and cytarabine are co-encapsulated and said mole ratio is maintained in the blood for at least four hours after administration to the subject.

13. A composition for parental administration to a subject which composition comprises liposomes having associated therewith daunorubicin and cytarabine, wherein the daunorubicin:cytarabine mole ratio is about 1:5 and wherein
   (a) the daunorubicin and cytarabine are co-encapsulated;
   (b) said mole ratio is maintained in the blood for at least four hours after administration to the subject;
   (c) the liposomes have a mean diameter of less than 250 nm; and
   (d) the composition comprises no therapeutic agents in addition to the daunorubicin and cytarabine.

14. The composition of claim 13, wherein the liposomes comprise DSPC, DSPG and cholesterol in a mole ratio of about 7:2:1.

* * * * *